United States Patent [19]

Fischer

[11] Patent Number: 5,316,541
[45] Date of Patent: May 31, 1994

[54] ENCLOSURE FOR SURGICAL PROCEDURES

[76] Inventor: William B. Fischer, 10203 Country Club Rd., Woodstock, Ill. 60098

[21] Appl. No.: 5,569

[22] Filed: Jan. 19, 1993

[51] Int. Cl.⁵ ..................... A61G 10/00; A61B 19/00
[52] U.S. Cl. ..................... 600/21; 128/849; 128/853; 128/917
[58] Field of Search .............. 600/21; 128/847, 849, 128/917, 853

[56] References Cited

U.S. PATENT DOCUMENTS

| | | |
|---|---|---|
| 2,403,400 | 7/1946 | Reyneirs . |
| 2,473,033 | 6/1949 | Letac . |
| 3,051,163 | 8/1962 | Trexler . |
| 3,051,164 | 8/1962 | Trexler . |
| 3,850,172 | 11/1974 | Cazalis . |
| 4,000,749 | 1/1977 | Buseo ................................. 600/21 |
| 4,275,719 | 6/1981 | Mayer . |
| 4,335,712 | 6/1982 | Trexler ............................... 600/21 |
| 4,367,728 | 1/1983 | Mutke ................................. 600/21 |
| 4,485,806 | 12/1984 | Akers .................................. 600/21 |
| 4,612,916 | 9/1986 | Akers et al. . |
| 4,950,222 | 8/1990 | Scott et al. . |
| 5,197,493 | 3/1993 | Grier-Idris ..................... 128/489 X |

FOREIGN PATENT DOCUMENTS

| | | |
|---|---|---|
| 851240 | 7/1949 | Fed. Rep. of Germany ........ 600/21 |
| 1118657 | 7/1968 | United Kingdom ................. 128/847 |
| 1581200 | 12/1980 | United Kingdom ................. 600/21 |

OTHER PUBLICATIONS

Edelman, "Safe surgery is no soak-through", Orthopedics Today, pp. 10–11 (Dec. 1992).
Hall, "Anti-virus gowns bring success to Warsaw Company", The Journal-Gazette, 2 pages (Dec. 6, 1992).
"CDC Recommends Infection-Control Procedures", Brochure of Glaxo Pharmaceuticals, pp. 2, 3 and 6 (Jun. 1992).
Sloan Sta-Dri Sales Letter and price list, Sloan Medical, a Division of Sloan Corporation, 2 pages (Nov., 1992).
Products catalog, Henry Schein, Inc., Port Washington, N.Y., p. 3 (1992).
Germfree Flexible Film Isolators.

*Primary Examiner*—Steven A. Bratlie
*Attorney, Agent, or Firm*—Leydig, Voit & Mayer

[57] ABSTRACT

An enclosure which can be sterile for performing surgical procedures and a method for its use is disclosed that protects medical personnel from being infected by the patient and the patient from being infected by the surgical environment. The enclosure consists of a tent defining an isolated cavity and having flexible sides at least portions of which are transparent with connected gloves for accessing tools contained within the isolated cavity, an adhesive assembly for securing the enclosure to a patient and a support structure for supporting the tent. The surgeon can operate on a patient by making an incision through the enclosure, the adhesive assembly and the patient's skin. The incision and, consequently, the patient's body fluids, are all contained within the isolated cavity defined by the enclosure. Since the enclosure is collapsible and inexpensive, the entire structure can be disposed of after the surgery. Moreover, the enclosure can be quite small depending on the nature of the procedure. Thus, the use of the invention greatly reduces the amount of sterilizing procedures and their attendant costs required before and after a surgery is performed.

21 Claims, 6 Drawing Sheets

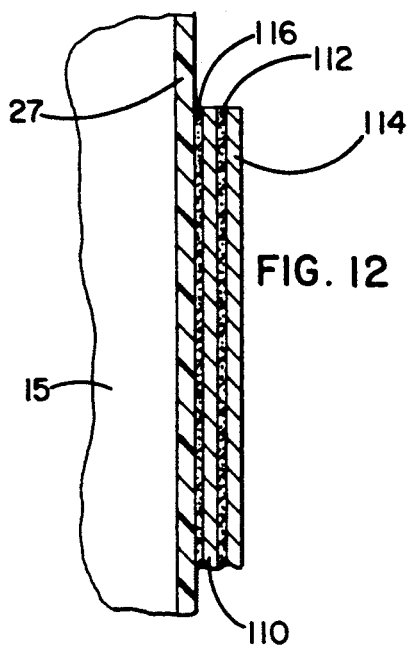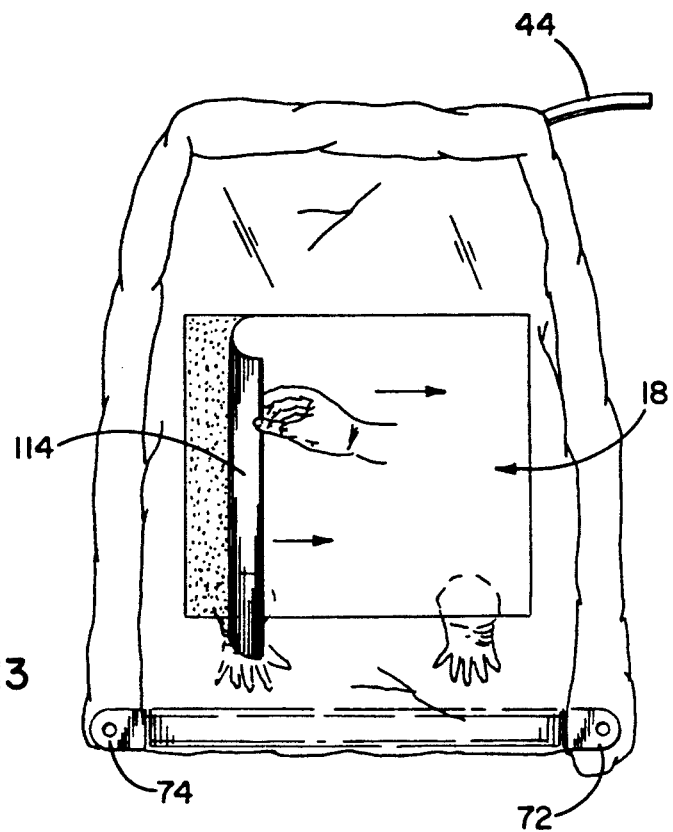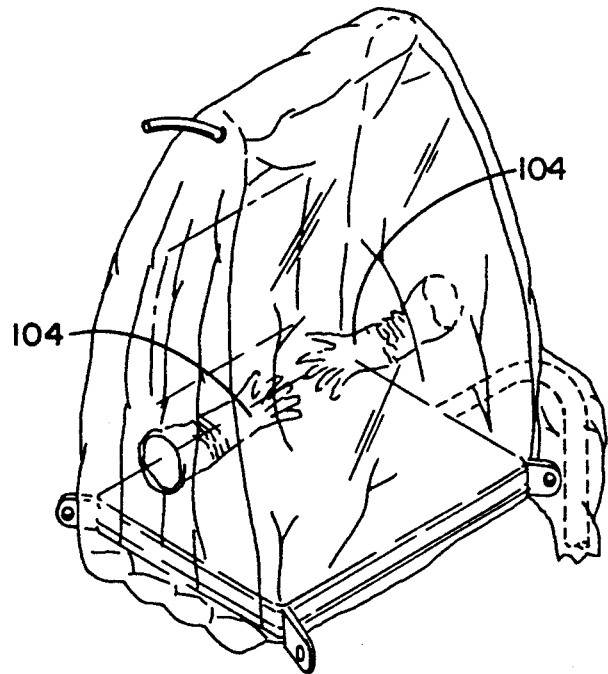

ENCLOSURE FOR SURGICAL PROCEDURES

FIELD OF THE INVENTION

This invention relates generally to surgical devices and more particularly to enclosures for use in surgical procedures.

BACKGROUND OF THE INVENTION

The safe and effective performance of surgical procedures has always required that special precautions be taken to ensure the sterility of the operating environment. These precautions have traditionally focused on protecting the patient from infection because during surgery their natural protective barrier, their skin, is violated to enable the operation. However, in recent years there has been great concern about the risks surgical procedures pose to the physicians and nurses who perform them. The spread of highly contagious and potentially deadly viruses such as the HIV virus has made surgical procedures more and more dangerous. Thus, the concern with sterility in the surgical environment has taken on a new twist. Now the medical profession needs to protect both patients and medical personnel from infection during an operation.

This dual concern has resulted in more and more drastic precautions. For instance, entire operating rooms and all the surgical equipment they contain must now be extensively sterilized between every use. Further, it now costs $180 just to drape a patient in sterile sheets for an operation. Since time-consuming and expensive steps such as these must now be taken just to prepare an operating room for a single surgical procedure, it is plain that these increased precautions have contributed to rising health care costs and helped fuel the health care crisis this country faces.

OBJECTS OF THE INVENTION

It is a general object of the invention to provide an improved enclosure for use in surgical procedures that protects medical personnel from exposure to any virus the patient might carry, and, at the same time protects the patient from infection. Accordingly, it is an object of the invention to provide an isolated environment for surgical procedures that has a limited predefined volume. It is yet another object of the invention to provide a method of performing a surgical procedure on an anatomical structure that maintains the patient's body fluids in isolation from the medical personnel before, during and after the procedure is performed.

It is a related object of the invention to eliminate the need for expensive and time-consuming sterilization of entire operating rooms before and after every operation. It is another object of the invention to provide a disposable enclosure that reduces the hazards faced by health care personnel both during and after surgical procedures performed on patients carrying dangerous viruses.

SUMMARY OF THE INVENTION

The present invention accomplishes these objectives and overcomes the drawbacks of the prior art by providing a disposable enclosure defining an isolated cavity in which an entire surgical procedure can be performed and by providing a method for utilizing the enclosure that isolates medical personnel from the patient's body fluids and other surgical wastes both while performing the procedure and while cleaning up after its completion. The enclosure is a collapsible transparent tent with flexible sides that includes a support structure that maintains the tent in a vertical position defining an isolated cavity. A pair of surgical gloves are either integrally formed in or sealed to the tent to enable a physician to insert his hands and manipulate sterile surgical tools that are contained within the enclosure. An adhesive assembly is also fixedly attached to the transparent tent's exterior. The exterior side of this adhesive assembly is covered with a pressure sensitive adhesive that is used to affix the tent to a patient's skin. Finally, the enclosure includes an access opening that allows a physician to pass instruments and other materials into and out of the isolated cavity during a procedure.

In use, the enclosure is first assembled such that the support structure holds the tent in an upright position. Next, the pressure sensitive adhesive of the adhesive assembly is exposed and pressed against the patient to affix the enclosure to the surgical site. The physician may then insert his/her hands into the gloves and manipulate the enclosed surgical tools to make an incision through the tent, adhesive assembly and the patient's skin and perform the procedure.

Since the adhesive assembly remains fixed to the patient throughout the procedure, the entire operation is performed in isolation from the operating room and the personnel involved in the procedure. As a result, the patient is protected from any contaminants present in the operating room. Furthermore, since the patient's blood, tissue and any viruses they happen to carry are also wholly contained within the enclosure's isolated cavity, the physicians and nurses are protected from any virus the patient carries. Consequently, the enclosure reduces the risk of infection that physicians and other medical personnel face in performing a procedure.

Moreover, at the completion of the procedure, the entire enclosure and any potentially hazardous materials it contains are disposed of through incineration or other means. The materials contained in the enclosure are never exposed to the operating room. Consequently, there is no reason to sterilize the entire operating room between each and every operation. Instead, a new enclosure is simply set up for the next procedure. Thus, the enclosure obviates the need to undertake time-consuming and highly expensive clean-up procedures and thereby reduces the overall cost of the operation. Thus, the present invention makes surgical procedures less expensive and safer to all participants by greatly reducing the time and efforts needed to ensure a safe operating environment.

These and other features and advantages of the invention will be more readily apparent upon reading the following description of the preferred embodiment of the invention and upon reference to the accompanying drawings wherein:

BRIEF DESCRIPTION OF THE DRAWINGS

FIG. 12 is a partial cross-sectional view of an adhesive assembly affixed to the enclosure taken along lines 12—12 of FIG. 4;

FIG. 13 is a rear elevational view of an enclosure similar to FIG. 4, but showing the exposure of the pressure sensitive adhesive layer; and, FIG. 14 is a left-front perspective view of a second alternative embodiment of the invention.

DESCRIPTION OF A PREFERRED EMBODIMENT

Figure 1:
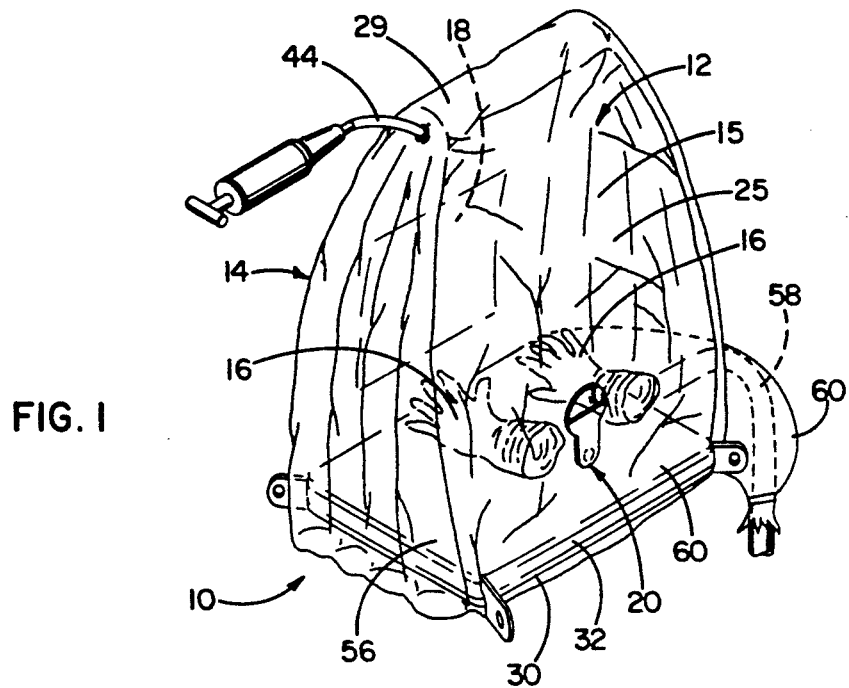
FIG. 1 is a left front perspective view of an enclosure constructed in accordance with the teachings of the invention.
Figure 2:
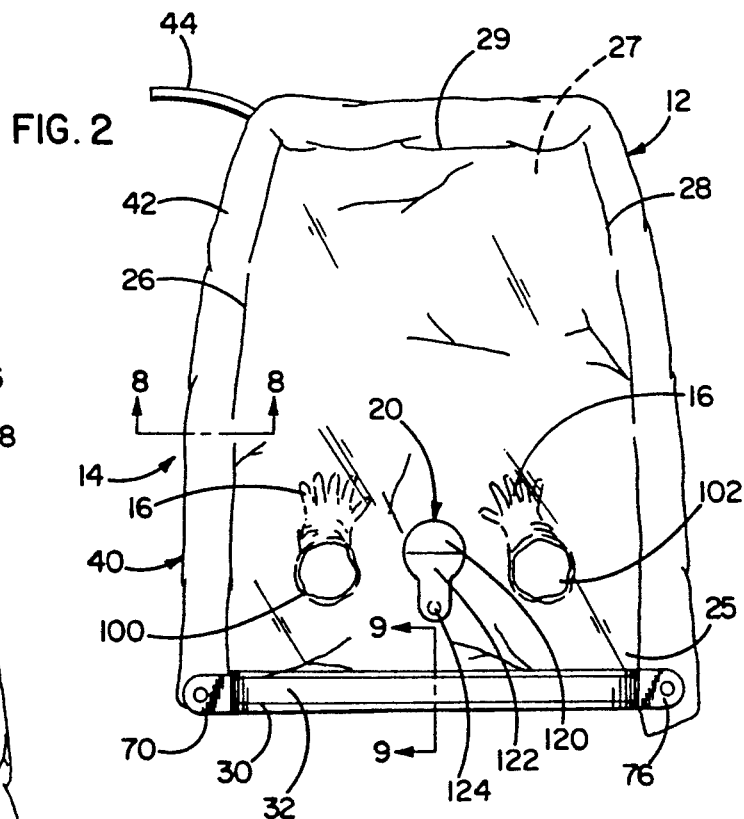
FIG. 2 is a front elevational view thereof.

Reference numeral 10 in FIG. 1 refers generally to an enclosure for surgical procedures constructed in accordance with the teachings of the invention. The enclosure provides an isolated environment for surgical procedures by defining an isolated cavity 15. As can be seen in FIG. 1 the enclosure comprises a transparent tent 12, a support structure 14, a pair of surgical gloves 16 sealed to the tent 12, an adhesive assembly 18, and an access portal assembly 20. As best seen in FIG. 2, tent 12 preferably has four sides 25, 26, 27, & 28 and a top 29 but no bottom. The tent's walls 25, 26, 27, & 28 and its top 29 are made from a flexible material such as plastic that will prevent the passage of fluids and air. These walls 25, 26, 27 & 28 and the top 29 are all sealed firmly together to increase this effect. The lowermost portion of the tent's walls 25, 26, 27 & 28 include a pocket 30 that carries an elastic band 32 that forms a circumference around the tent's bottom opening (not shown) and whose significance will be explained momentarily.

Since the tent 12 is constructed from a flexible material it will collapse upon itself without a support means. Consequently, the tent is provided with a support structure 14 as shown in FIG. 1. In the preferred embodiment of the invention, this support structure 14 comprises a second layer 40 of plastic firmly sealed to the top 29 and the two side walls 26, 28 of the tent 12. As best seen in FIG. 2, this second layer 40 of plastic is sealed to the tent 12 such that it forms an air-tight pocket 42 around the top 29 and sides 26, 28 of the structure. This pocket 42 is provided with an air stem 44 with a pneumatic sealing core or an associated check valve which can be used in inflating the pocket 42 with a suitable gas such as air and will prevent the pocket 42 from inadvertently deflating at all other times.

Figure 8:
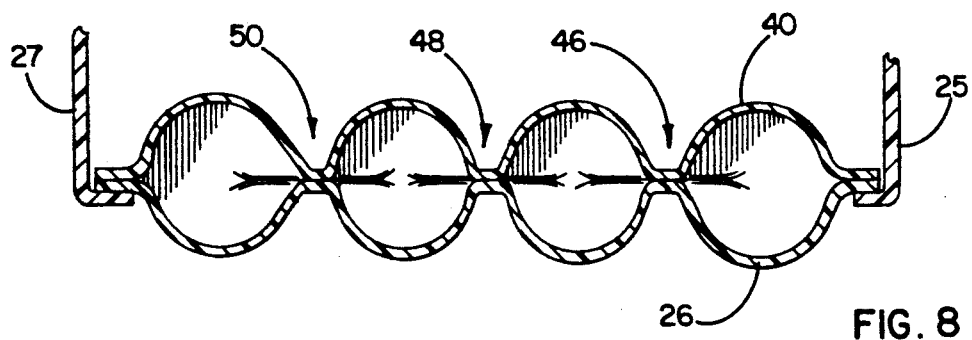
FIG. 8 is a cross-sectional view of the left side of the enclosure taken along lines 8—8 in FIG. 2.

When sufficiently inflated, the pocket 42 forms a rigid support structure 14 that holds the flexible sides of the tent 12 in an upright position defining the isolated cavity 15. As can best be seen in FIG. 3, in order to increase the rigidity of this support structure 14, the second layer 40 of plastic is preferably sealed to the sides 26, 28 of the tent in three seams 46, 48, 50. As illustrated in FIG. 8, these seams 46, 48, 50 form three chambers in the pocket 42 giving the support structure 14 an air-mattress like quality and thereby increasing the support structure's rigidity. It should be noted that in order to provide a better interface between the top and side portions of the pocket 42, the center seam 48 is preferably 1½ inches shorter than the side seams 46, 48 on both sides of the pocket 42.

Figure 11:
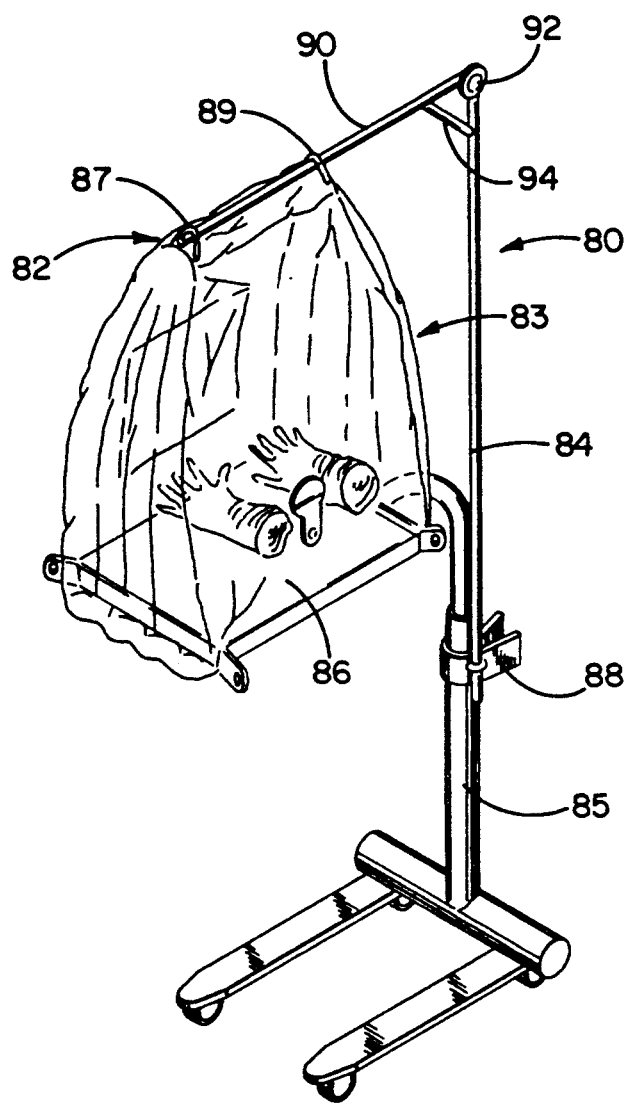
FIG. 11 is a right front perspective view of an alternative embodiment of the invention.

While the invention is preferably constructed with the inflated support structure 14 described above, it will be observed by those skilled in the art that support structures of other configurations may also be appropriate. For example, as illustrated in FIG. 11 the enclosure 80 could also be constructed with a rod and loop support structure 82. In this embodiment, the tent 83 does not include a second layer 40 of plastic or an inflatable pocket 42. Instead, it includes two fabric loops 87, 89 on the top of the tent 83. Further, the enclosure 80 is provided with a vertically extending pole 84 attached to the Mayo stand 85 supporting the surgical tray 86 by a clamp 88 or other attachment means. A horizontal pole 90 is connected to the top of the vertical pole 84 by a hinge 92 and held in a horizontal position by a support beam 94 wedged between the vertical and horizontal poles 84, 90. The fabric loops 87, 89 are slid over the horizontal pole 90 and the tent 83 is thereby held in a vertical position. It should be noted that a hook and dolly system is another one of the many support structures that could be substituted for the inflated pocket or rod and loop structures with more or less equal success.

Figure 6:
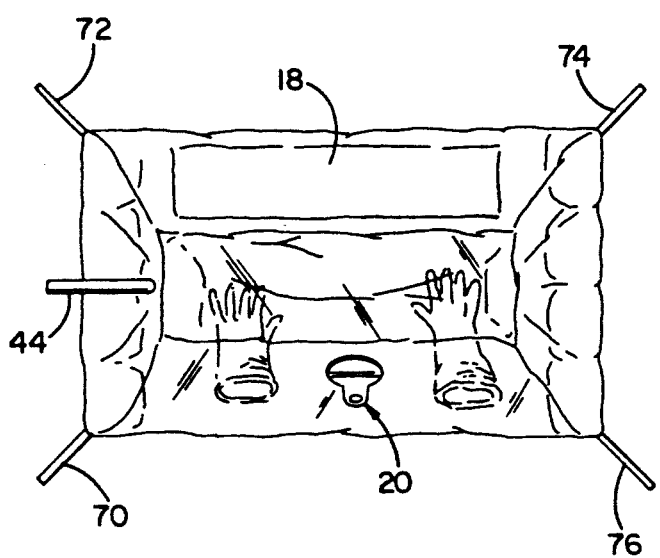
FIG. 6 is a top plan view thereof.

As previously mentioned, the tent 12 preferably does not include a bottom. Instead, a tray 56 connected to a Mayo stand 58 preferably forms the bottom of the enclosure 10. As shown in FIG. 1, the elastic band 32 can be stretched to fit around the tray 56. The elastic band 32 will then hold the sides 25, 26, 27 & 28 of the tent 12 snugly against the tray 56 and thereby form a completely sealed enclosure 10. It should be noted that the tray 56 separates the sides of the tent 12 to their maximum extent such that the tent 12 attains its maximum interior volume. It should also be noted that in order to facilitate the attachment of the tent 12 to the tray 56, the tent 12 is preferably constructed with finger tabs 70, 72, 74, & 76 on each of its bottom corners that can be gripped during the assembly procedure as shown in FIG. 6.

Figure 7:
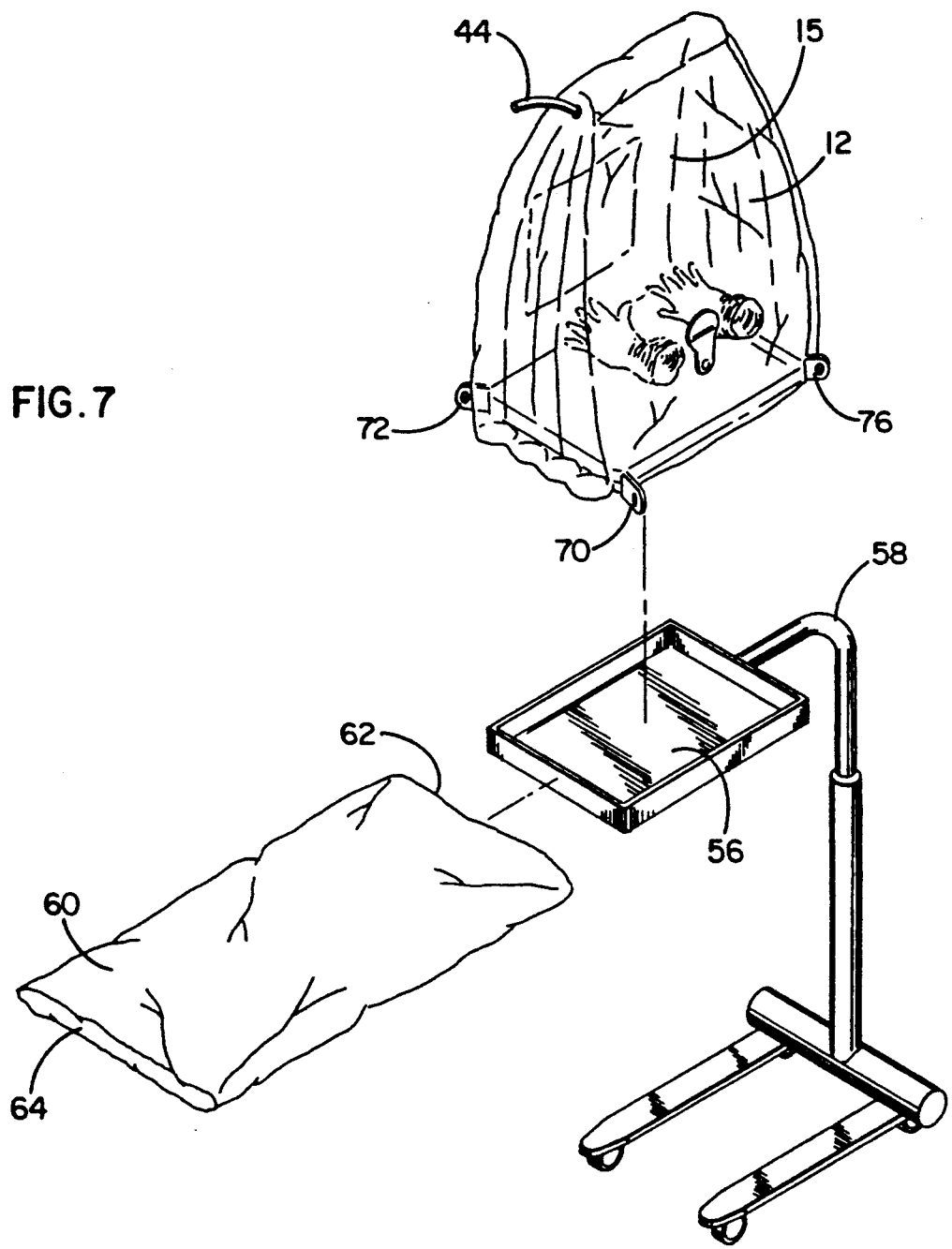
FIG. 7 is an exploded view thereof illustrating the assembly technique for creating an enclosure having an isolated cavity.

In order to minimize the clean-up procedures required after a procedure is performed, the surgical tray 56 is preferably covered with a cover 60 before the tent 12 is attached. As best seen in FIG. 7, this cover 60 is preferably a sack whose open end 62 is larger than its closed end 64 and whose length is roughly twice as long as the length of the surgical tray 56. Moreover, the cover 60 is preferably made of the same material as the tent 12 and, consequently, it will not transmit either fluids or air. The cover 60 thus prevents the tray 56 from coming into contact with any of the patient's body fluids during a surgical procedure. After the procedure is completed, the tent 12 can be collapsed onto the cover 60 and the cover 60 can be carefully withdrawn from the tray in a manner that turns the cover 60 inside out thereby retaining the tent 12 and all the disposable surgical by-products inside the cover 60. The cover 60 can then be sealed and disposed of without ever exposing the operating room or the medical personnel cleaning up after the procedure to the materials held in the enclosure.

As previously mentioned, the enclosure 10 is provided with a pair of surgical gloves 16 that are sealed to the tent 12. As illustrated in FIG. 2, the gloves 16 are preferably sealed into two apertures 100, 102 in the front wall 25 of the tent 12. However, it will be appreciated by those skilled in the art that the gloves 16 could also be integrally formed into the wall 25. Moreover, it will also be appreciated that the gloves could be sealed into any surface of the tent 12 that will facilitate access to the enclosure and the patient. For example, as shown in FIG. 14, the gloves 104 could also be placed in the side walls of the enclosure to make it easier for a physician with widely spaced shoulders to comfortably use the invention.

Figure 3:
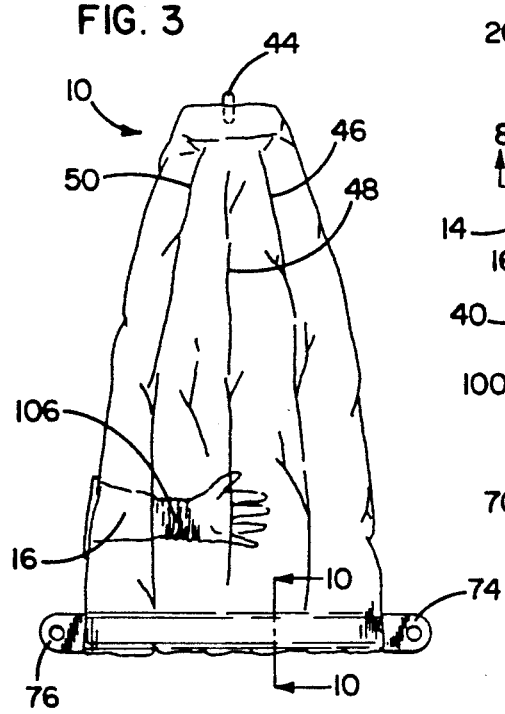
FIG. 3 is a right side elevational view thereof.

As best seen in FIG. 3, the gloves 16 are constructed with an expandable, accordion structure 106. This accordion structure 106 in effect increases the overall length of the gloves 16 and thereby enables a physician utilizing the enclosure 10 to perform a surgical procedure within the isolated cavity 15 without feeling constrained by the attached tent walls. Alternatively, the gloves 16 can be constructed without the accordion structure 106. However, in this embodiment the gloves must be sufficiently long to enable the physician sufficient latitude to perform an operation.

Figure 4:
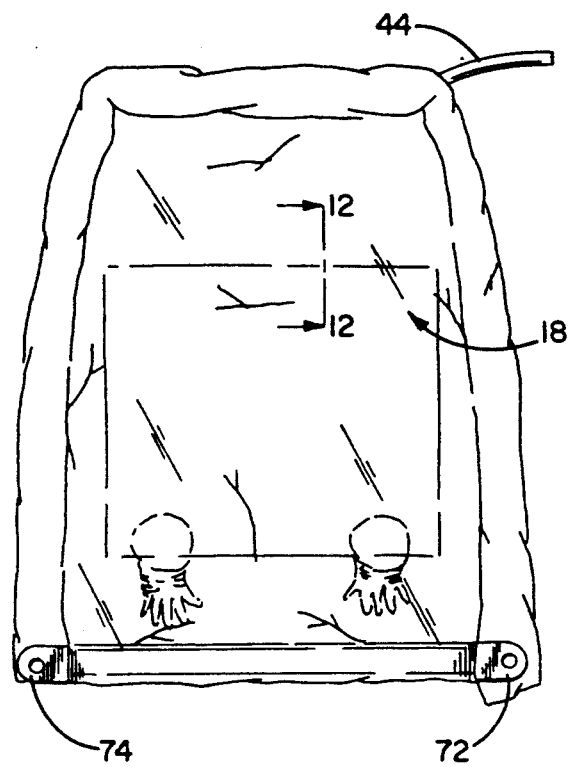
FIG. 4 is a rear elevational view thereof.
Figure 5:
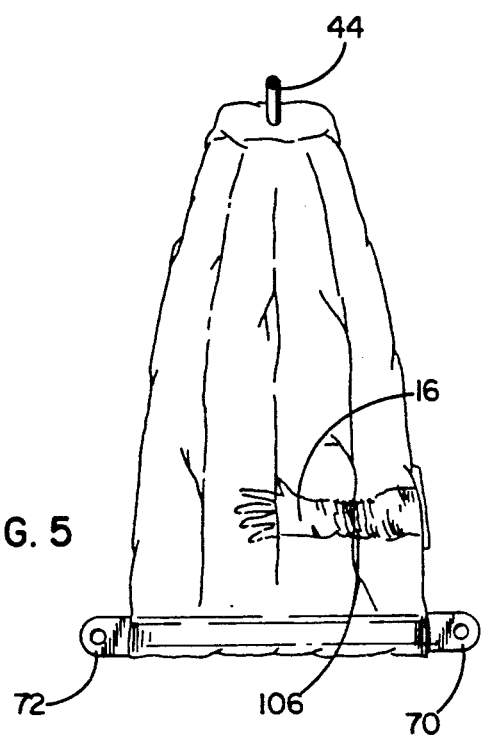
FIG. 5 is a left side elevational view thereof.

In accordance with an important aspect of the invention, an adhesive assembly 18 is fixedly attached to the back wall 27 of the tent 12 as illustrated in FIG. 4. The adhesive assembly 18 comprises a sheet of plastic 110, a pressure sensitive adhesive 112 and a paper cover 114. The pressure sensitive adhesive 112 holds the paper covering 114 and the plastic sheet 110 together as a unit. As illustrated in FIG. 12, the adhesive assembly 18, is attached to the tent's back wall 27 by an adhesive 116 such as 3M's Pressure Sensitive Adhesive No. 4268-NF such that there are five layers of materials between the isolated cavity 15 and the patient. Since when the physician performs a procedure with the enclosure 10, he/she first removes the paper covering 114 as illustrated by FIG. 13 and then presses the exposed adhesive layer 112 against the patient's skin, the adhesive layer 112 will keep the plastic sheet 110, and consequently the enclosure 10, firmly attached to the patient throughout the procedure.

It will be appreciated by those skilled in the art that although the adhesive assembly 18 has been described as utilizing a plastic sheet 110 with an adhesive 112 protected by a paper cover 114, the assembly 18 could take alternative forms. For instance, the assembly 18 could comprise merely the adhesive 112 applied directly to the tent 12 wherein the adhesive 112 is again protected by a paper cover 114 until use. If this approach is followed, only the wall 27 of the tent 12 and the adhesive layer 112 will be between the patient and the isolated cavity 15 before the incision is made because the paper cover 114 will have been removed to attach the tent 12 to the patient.

According to another important aspect of the invention, the enclosure 10 is provided with an access portal assembly 20. As shown in FIG. 2, this portal assembly 20 comprises a semi-circular aperture 120, a flap 122 and a sealing means 124. The aperture 120 is an opening in the front wall 25 of the tent 12 located near the bottom of the enclosure 10 so that any instruments that need to be added to the isolated cavity 15 during a procedure can be dropped in without damaging the enclosure 10 or the instruments. Although the access portal assembly 20 has been described as being located in the front wall 25 of the tent 12, it will be appreciated by those skilled in the art that the portal can be placed in any location that will enhance the operation of the enclosure 10 in a surgical procedure.

The flap 122 is permanently sealed to the exterior of the tent 12 nearly all the way around the aperture 120. However, the lower portion of the flap 122 is not permanently sealed but is instead held tightly against the tent wall by the sealing means 124. In the preferred embodiment, the sealing means 124 consists of a patch that latches through a hook and loop configuration such as Velcro on the tent wall 25 and a corresponding patch on the flap 122 that can be pressed together to form the seal. However, it will be appreciated that other temporary sealing means might also be appropriate. The portal assembly 20 enhances the usefulness of the enclosure 10 since should it be necessary to gain access to the isolated cavity 15, the physician need only detach the hook and loop patches and lift the flap 122. This feature allows a physician to pass materials either into or out of the enclosure 10 without difficulty.

In accordance with an important aspect of the invention, the enclosure 10 can be provided with a sealable envelope that is constructed of the same material as the tent 12 and is small enough to pass through the access portal assembly 20. This envelope can be used to receive tissue samples or surgical tools and can be carefully passed out through the access portal assembly 20 during a procedure without disrupting the entire enclosure 10. Should the envelope contain surgical instruments when it is removed from the enclosure 10, it can be autoclaved or sterilized by some other appropriate means without removing the instrument from the package.

In order to manufacture the enclosure 10, the tent 12 is first formed from four sheets of either 2 or 4 mil poly vinyl. One of these four plastic sheets is long enough to form the front side 25, the back side 27 and the top 29 of the tent 12 when folded. This long sheet is first placed on a flat surface. Next, a 13"×14" area is marked on the exterior of the back side 27 of the tent 12. This area is then cleaned with isopropyl alcohol and dried. Next, 0.5 cc of a pressure sensitive adhesive such as that sold by 3M under the product number 4268-NF is poured on the cleaned area and on the plastic sheet 110 of adhesive assembly 18. Both of these adhesive covered surfaces are then rolled with a 3" wide sheep's skin roller until a very thin, prickly grain is achieved. After a five minute wait, the adhesive will turn clear. Then, the adhesive covered surfaces are approximated smoothly with a wall paper roller. At this point, the two apertures 100, 102 that are to receive the gloves 16 and the aperture 120 for the access portal assembly are cut into the front wall 25 of the plastic sheet.

Figure 9:
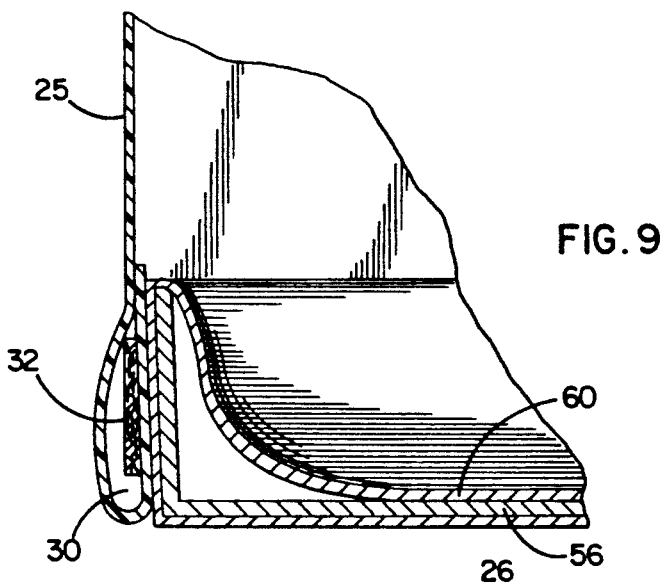
FIG. 9 is a partial cross-sectional view of the enclosure taken along lines 9—9 of FIG. 2.
Figure 10:
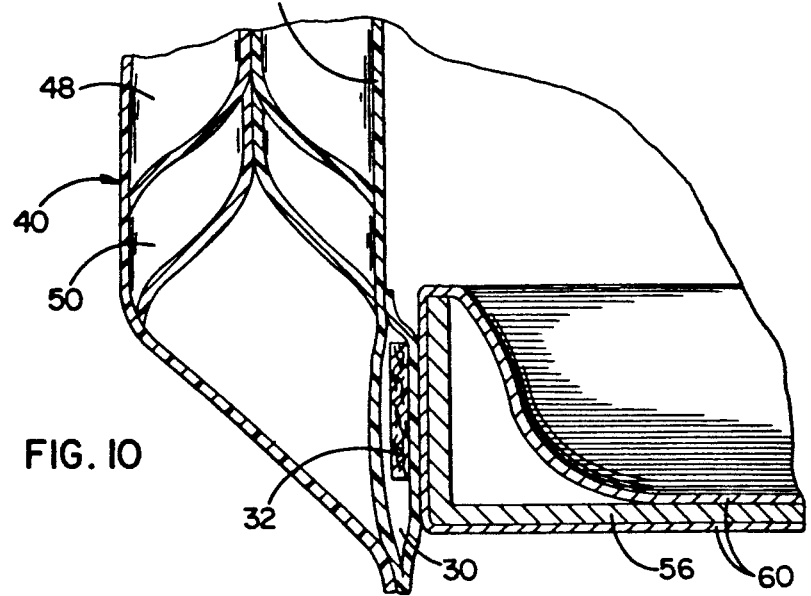
FIG. 10 is a partial cross-sectional view of the enclosure taken along lines 10—10 of FIG. 3.

Once the apertures are formed and the adhesive assembly 18 is secured, the two plastic sheets that are to form the left and right sides 26, 28 of the tent 12 are welded to the folded sheet with a seam pre-coating. Next, the remaining plastic sheet is welded to the left side 26, the top 29, and the right side 28 of the tent 12 to form the double layer support structure 14. As shown in FIGS. 9 and 10, the bottoms of the sides 25, 26, 27, & 28 can then be rolled and welded into a pocket 30 housing the elastic band 32.

The final steps of the manufacturing process entail sealing the flap 122 of the access portal assembly 20 to the front wall 25; sealing the gloves 16 to the tent 12 such that they extend inwardly through apertures 100, 102; attaching the air stem 44 with its core or associated check valve to the air pocket 42; attaching the finger tabs 70, 72, 74 & 76 to the bottom corners of the tent 12; and attaching the sealing means 124 to the access portal assembly 20. Finally, the cover 60 is formed by cutting a sheet of poly vinyl of the appropriate dimensions, folding it and sealing the sides. The entire enclosure 10 and cover 60 can then be packaged and sterilized through autoclaving or some other appropriate method.

In use, the physician or other personnel can utilize the following method to ensure the patient's body fluids are isolated before, during and after a surgical procedure is performed. First the user opens the package containing the enclosure and removes the cover 60. The cover 60 is then drawn around the tray 56 until the sealed end abuts the tray 56 as shown in FIG. 10. Since the cover 60 is roughly twice the length of the tray 56, a significant amount of excess cover 60 left over. In the preferred embodiment, this excess extends down the support post of the Mayo stand 58 where it is secured through clamping, tying or other means.

After whatever surgical instruments that are to be used in the procedure are placed on the covered tray 56, the tent 12 is removed from its packaging. Using the finger tabs 70, 72, 74 & 76, the physician then stretches the elastic band 32 around the tray 56 such that the band 32 compresses the cover 60 against the tray 56 and thereby creates a seal between the tent 12 and the tray 56 as shown in FIGS. 9 and 10. At this point, the tent 12 is limp due to the flexibility of its sides 25, 26, 27, & 28. Consequently, the next step is to use the air stem 44 to inflate the support structure 14 with an air pump as shown in FIG. 1. However, it will be appreciated that various inflation means such as a $CO_2$ cartridge or a nitrogen pressure tank might also be appropriate for this step.

After the support structure 14 is inflated such that the tent 12 defines the isolated cavity 15, the paper cover 114 is removed as shown in FIG. 13. This exposes the pressure sensitive adhesive 112 of the adhesive assembly 18 which is then affixed to the patient at the point of surgery. The physician then inserts his/her hands into the gloves 16 and manipulates the surgical instruments contained in the isolated cavity 15. Since the plastic sheet 110 of the adhesive assembly 18, the back wall 27 of the tent 12, and the adhesives used to affix the adhesive assembly 18 to the patient and to the tent 12 are all clear, the physician may view the patient through the assembly 18 without difficulty. Consequently, the physician can make an incision through the enclosure 10 and the patient's skin at the appropriate site. The procedure is then performed with all of the patient's body fluids contained within the isolated cavity 15.

When the procedure is completed, any non-disposable surgical instruments and tissue samples are carefully removed through the access portal assembly 20 and the support structure 14 is deflated. The cover 60 is then carefully pulled over the tent 12 such that the cover 60 turns inside out thereby retaining the tent 12 and surgical wastes in a disposable sack. The cover 60 and all its contents is then incinerated or disposed of by some other appropriate means.

It will be appreciated by those skilled in the art that although the invention has been described for use in a surgical procedure, the enclosure can also be used in many other ways. For instance, the enclosure can be used in dental procedures to protect dentists and dental personnel from exposure to the body fluids and viruses of their patients. Using the enclosure in other procedures such as this requires modifications to the enclosure's access portal assembly, its tent, and its adhesive assembly. For instance, one skilled in the art can modify the enclosure to be more conducive to procedures performed on a patient's abdomen by adding a plastic bottom carrying the adhesive assembly to the tent.

I claim:

1. A surgical enclosure for preventing infection and the transmission of viruses during a procedure on an anatomical structure comprising:
   a disposable collapsible tent defining a volume for containing surgical instruments and having at least portions that are transparent;
   a support structure supporting said tent such that said tent is held in a position that defines said volume;
   at least one pair of surgical gloves extending inwardly into said volume and forming a seal with said tent for permitting access to and manipulation of surgical instruments in said volume; and,
   adhesive means operatively connected to the exterior of said tent; said adhesive means defining a sealed access area which may be cut to provide an access opening for performing said surgical procedure from inside said volume.

2. An enclosure as defined in claim 1 wherein said tent includes an access portal assembly for passing instruments and materials into and out of said volume during said procedure.

3. An enclosure as defined in claim 1 wherein said tent is constructed from poly vinyl.

4. An enclosure as defined in claim 1 wherein said tent includes a bottom formed by a tray and means for removably sealing said tent to said tray.

5. An enclosure as defined in claim 4 wherein said tray is covered by a cover and said sealing means for sealing said tent to said tray is an elastic band carried by said tent.

6. An enclosure as defined in claim 5 wherein said cover is a sack for containing said tent for disposal.

7. An enclosure as defined in claim 6 wherein said cover is constructed from the same material as said tent.

8. An enclosure as defined in claim 5 wherein said tent has four generally rectilinear walls including tabs adjacent to the bottom corners of said walls for gripping when stretching said elastic band of said tent around said tray.

9. An enclosure as defined in claim 1 wherein said tent includes an inflatable, self-sustaining double wall support structure which forms said support structure supporting said tent.

10. An enclosure as defined in claim 9 wherein said double wall support structure includes a fluid access for inflation.

11. An enclosure as defined in claim 10 wherein said double wall support structure includes a check valve in association with said fluid access to maintain said inflation.

12. An enclosure as defined in claim 9 wherein said double wall support structure includes a plurality of generally vertical passageways thereby dividing said double wall support structure into sections for providing stiffness.

13. An enclosure as defined in claim 1 wherein said support structure suspends said enclosure and comprises:
   a stand having a frame portion positionable above said tent; and
   fasteners on the top of said tent, said fasteners engaging said frame portion and positioning said tent to define said interior volume.

14. An enclosure as defined in claim 1 wherein said enclosure has a plurality of walls and said gloves are located in a front wall of said tent and said adhesive means is located in a back wall of said tent.

15. An enclosure as defined in claim 14 wherein said gloves are dimensioned to extend beyond said adhesive means from inside said volume during said surgical procedure.

16. An enclosure as defined in claim 1 wherein said tent includes a plurality of walls, said gloves are located in opposing side walls of said tent and said adhesive means is located in a back wall of said tent.

17. An enclosure as defined in claim 16 wherein said gloves are dimensioned to extend beyond said adhesive means from inside said volume during said procedure.

18. An enclosure as defined in claim 1 wherein said adhesive means comprises a surgical drape having a pressure sensitive adhesive on one side, an opposed surface secured to the exterior of said tent on its opposite side, and a protective cover sheet releasably affixed to said pressure sensitive adhesive whereby said cover sheet may be removed, said surgical drape can be positioned for said procedure, and an incision can be made through said tent and said surgical drape to perform said procedure.

19. An enclosure as defined in claim 2 wherein said access portal assembly comprises:
an aperture in said tent covered by a flap permanently sealed around most of said aperture and including a closure means for temporarily sealing the unsealed section of said flap.

20. An enclosure as defined in claim 19 wherein said closure means comprises a hook and loop patch that holds said flap fixedly closed and said flap is constructed of the same material as said tent.

21. A method of performing a surgical procedure in an isolation cavity of limited volume and maintaining isolation for disposal comprising the steps of:
adhesively securing an external area of a flexible enclosure to a patient;
cutting an aperture through said enclosure within said area;
performing a surgical procedure on said patient through said aperture;
detaching said enclosure from said patient; and,
folding said enclosure into a receptacle portion thereof for disposal without exposing the contents of said enclosure to the environment.

* * * * *